(12) United States Patent
Kim et al.

(10) Patent No.: US 9,970,933 B2
(45) Date of Patent: May 15, 2018

(54) METHOD FOR MANUFACTURING MULTIPLE-DIAGNOSIS MEMBRANE SENSOR BY USING SCREEN PRINTING

(71) Applicant: INGIBIO, LTD., Gwangju (KR)

(72) Inventors: Min-Gon Kim, Gwangju (KR); Hyou-Arm Joung, Gwangju (KR); Jun-Hyoung Ahn, Daejeon (KR); Ho-Jun Suk, Incheon (KR)

(73) Assignee: INGIBIO, LTD., Gwangju (KR)

( * ) Notice: Subject to any disclaimer, the term of this patent is extended or adjusted under 35 U.S.C. 154(b) by 830 days.

(21) Appl. No.: 14/350,278

(22) PCT Filed: Oct. 5, 2012

(86) PCT No.: PCT/KR2012/008087
§ 371 (c)(1),
(2) Date: Apr. 7, 2014

(87) PCT Pub. No.: WO2013/051890
PCT Pub. Date: Apr. 11, 2013

(65) Prior Publication Data
US 2014/0287439 A1  Sep. 25, 2014

(30) Foreign Application Priority Data

Oct. 6, 2011 (KR) .................. 10-2011-0101671
Oct. 5, 2012 (KR) .................. 10-2012-0110524

(51) Int. Cl.
*G01N 33/569* (2006.01)
*G01N 33/558* (2006.01)
*G01N 33/543* (2006.01)

(52) U.S. Cl.
CPC ..... *G01N 33/558* (2013.01); *G01N 33/54366* (2013.01); *G01N 33/56911* (2013.01); *G01N 33/56916* (2013.01)

(58) Field of Classification Search
CPC ............... G01N 33/56911; G01N 33/56916
See application file for complete search history.

(56) References Cited

U.S. PATENT DOCUMENTS 3,616,258 A * 10/1971 Kronish ............... C12Q 1/04
                                                                 422/420
4,017,261 A *  4/1977 Svoboda ............. C12Q 1/28
                                                                 422/421
(Continued)

FOREIGN PATENT DOCUMENTS

KR        20010106902 A     12/2001

OTHER PUBLICATIONS

Andres W. Martinez et al., Diagnostics for the Developing World: Microfluidic Paper-Based Analytical Devices, Jan. 1, 2010, pp. 3-10, vol. 82, No. 1.
(Continued)

*Primary Examiner* — Scott Long
*Assistant Examiner* — Gary E Holliden
(74) *Attorney, Agent, or Firm* — Hauptman Ham, LLP

(57) ABSTRACT

Provided is a method for manufacturing a multiple-diagnosis membrane sensor provided with multiple channels by using screen printing, and more specifically, to a method for manufacturing a membrane sensor capable of performing multiple-diagnosis by screen-printing hydrophobic ink on a membrane to form multiple channels.

The membrane sensor according to the present invention may enable mass-production of sensors and secure reliability of detection by forming the plurality of channels on the membrane by a simple method.

9 Claims, 4 Drawing Sheets

2-channel NC membrane 4-channel NC membrane

(56) References Cited

U.S. PATENT DOCUMENTS

| | | | | |
|---|---|---|---|---|
| 5,571,684 | A | * | 11/1996 | Lawrence ............... C12Q 1/34 422/504 |
| 6,478,938 | B1 | | 11/2002 | Paek et al. |
| 6,733,655 | B1 | * | 5/2004 | Davies ................... C12Q 1/001 205/775 |
| 6,924,153 | B1 | * | 8/2005 | Boehringer .......... G01N 33/558 422/420 |
| 9,829,488 | B2 | * | 11/2017 | Derda .................. G01N 33/548 |
| 2002/0001854 | A1 | * | 1/2002 | Lee ....................... B01L 3/5023 436/518 |
| 2002/0072124 | A1 | * | 6/2002 | Khan ............... G01N 33/54366 436/95 |
| 2003/0073073 | A1 | * | 4/2003 | Wolde-Mariam .... G01N 33/558 435/5 |
| 2003/0166261 | A1 | * | 9/2003 | Sompuram ...... G01N 33/54386 435/287.2 |
| 2004/0053419 | A1 | * | 3/2004 | Keizer ................. G01N 33/558 436/169 |
| 2006/0193746 | A1 | * | 8/2006 | Lee .................... G01N 21/8483 422/400 |
| 2006/0267005 | A1 | | 11/2006 | Kawase et al. |
| 2007/0053962 | A1 | * | 3/2007 | Clark ....................... A61L 15/42 424/445 |
| 2007/0122873 | A1 | * | 5/2007 | Colpas ..................... C12Q 1/04 435/34 |
| 2007/0141655 | A1 | * | 6/2007 | Yee ................. G01N 33/56911 435/7.93 |
| 2008/0003687 | A1 | * | 1/2008 | Satoh ..................... G01N 21/78 436/169 |
| 2009/0145754 | A1 | * | 6/2009 | Yang .................. G01N 33/5438 204/403.02 |
| 2010/0120073 | A1 | * | 5/2010 | Hanson ............ G01N 33/56911 435/7.33 |
| 2011/0105360 | A1 | * | 5/2011 | Derda .................. B01J 19/0046 506/10 |
| 2012/0020839 | A1 | * | 1/2012 | Fuerst ................... B01L 3/5023 422/82.05 |
| 2012/0135509 | A1 | * | 5/2012 | Hall ....................... C12Q 1/001 435/287.1 |
| 2017/0363577 | A1 | * | 12/2017 | Reid .................... G01N 27/453 |

OTHER PUBLICATIONS

Yao Lu et al., Fabrication and Characterization of Paper-Based Microfluidics Prepared in Nitrocellulose Membrane by Wax Prinitng, Jan. 1, 2010, published on web Aug. 22, 2008, pp. 329-335, vol. 82, No. 1.

Andres W. Martinez et al., Flash: A Rapid Method for Prototyping Paper-Based Microfluidic Devices, Article, 2008, published on web Aug. 22, 2008.

Koji Abe et al., Inkjet-Printed Microfluidic Multianalyte Chemical Sensing Paper, Sep. 15, 2008, published on web Aug. 13, 2008 pp. 6928-6934, vol. 80, No. 18.

Andres W. Martinez et al., Simple Telemedicine for Developing Regions: Camera Phones and Paper-Based Microfluidic Devices for Real-Time, Off-Site Diagnosis, May 15, 2008, published on web Apr. 11, 2008, pp. 3699-3707, vol. 80, No. 10.

International Search Report dated Mar. 29, 2013 for PCT/KR2012/008087.

* cited by examiner

EXAMPLE 1    EXAMPLE 2    EXAMPLE 3

UNIT:ng/ml

FIG. 8

METHOD FOR MANUFACTURING MULTIPLE-DIAGNOSIS MEMBRANE SENSOR BY USING SCREEN PRINTING

CROSS REFERENCE TO RELATED APPLICATION

This application claims the priority of Korean Patent Application 10-2011-0101671 filed on Oct. 6, 2011 and Korean Patent Application No. 10-2012-0110524 filed on Oct. 5, 2012 in the Korean Patent and Trademark Office. Further, this application is the National Phase application of International Application No. PCT/KR2012/008087 filed on Oct. 5, 2012, which is incorporated herein by reference in its entirety.

TECHNICAL FIELD

The present invention relates to a method for manufacturing a multiple-diagnosis membrane sensor provided with multiple channels by using screen printing, and more specifically, to a method for manufacturing a membrane sensor capable of performing multiple-diagnosis by screen-printing hydrophobic ink on a membrane to form multiple channels.

BACKGROUND ART

A strip diagnosis sensor has been widely used after a pregnancy diagnostic kit was developed in 1976. Currently, the strip diagnosis sensor has been widely commercialized as a technology for early diagnosing various diseases. As an example of a strip sensor most widely used, there is a strip sensor using an immune chromatography method using a nitrocellulose membrane. This strip sensor may be easily mass-produced, conveniently used, and cheaply manufactured. Generally, a manufacturing cost, productivity, an easy measurement method, and the like, in addition to sensitivity and reproducibility are known as important factors for using a diagnosis biosensor. In addition, a need for a technology capable of simultaneously diagnosing various diseases through only a one-time measurement has been gradually emphasized. Therefore, in the case of devising a method of easily printing multiple patterns on a membrane widely used in a diagnosis biosensor to manufacture a strip sensor, among various diagnosis bio sensors including lateral flow assay (LFA), a strip sensor capable of performing multiple-diagnosis may be mass-produced.

Recently, research into a technology of printing a microfluidic channel, or the like, onto a membrane using wax, paraffin, or the like to manufacture a sensor has been actively conducted (Diagnostics for the Developing World: Microfluidic Paper-Based Analytical Devices, *Anal. Chem.*, 2010, 82 (1), pp 3-10; Inkjet-printed microfluidic multianalyte chemical sensing paper, *Anal. Chem.*, 2008, 80, pp 6928-6934; FLASH: A rapid method for prototyping paper-based microfluidic devices, *Lab Chip*, 2008, 8, pp 2146-2150; Simple telemedicine for developing regions: Camera phones and paper-based microfluidic devices for real-time, off-site diagnosis, *Anal. Chem.*, 2008, 80, 3699-3707; Fabrication and characterization of paper-based microfluidics prepared in nitrocellulose membrane by wax printing, *Anal. Chem.*, 2010, 82, pp 329-335).

The microfluidic channel sensor as described above has advantages that the microfluidic channel sensor may be simply used, cheap, and mass-produced, but there is a difficulty in that as an inkjet printing technology is used, a composition of used ink should be optimized.

Therefore, if a method of applying a microfluidic channel manufacturing technology to the strip sensor to manufacture multiple channels is easy and simple in view of mass production, a multiple channel strip sensor capable of cheaply and easily performing measurement may be manufactured.

DISCLOSURE

Technical Problem

The present invention has been made in an effort to provide a method for manufacturing a multiple-diagnosis membrane sensor capable of mass producing the multiple-diagnosis membrane sensor by screen-printing on a membrane.

Technical Solution

According to an aspect of the present invention, there is provided a method for manufacturing a multiple channel membrane sensor including: screen printing hydrophobic ink onto a membrane in which a water soluble sample flows to form multiple channels.

The membrane may be made of one kind or more of nitrocellulose, nylon, polysulfone, polyethersulfone, polyvinylidene fluoride (PVDF).

As the hydrophobic ink, one kind or more selected from a silver paste, a carbon paste, a platinum paste, a ceramic paste, and wax may be used, and the hydrophobic ink may contain one kind or two kinds or more organic solvents selected from alcohols having 1 to 6 carbon atoms, dimethylformamide (DMF), dimethyl sulfoxide (DMSO), and acetone.

According to another aspect of the present invention, there is provided a membrane sensor using a lateral flow including: multiple channels formed by screen printing hydrophobic ink on a surface of a membrane.

The membrane sensor further include a sample pad, a conjugation pad, an absorption pad on the membrane.

The sample pad or absorption pad may be made of at least one kind selected from cellulose, polyester, polypropylene, and glass fiber.

The conjugation pad may be made of at least one kind selected from cellulose, polyester, polypropylene, glass fiber, nitrocellulose, nylon, polysulfone, polyethersulfone, and polyvinylidene fluoride (PVDF).

The signal generation material may be metal nanoparticles, quantum dot nanoparticles, magnetic nanoparticles, an enzyme, an enzyme substrate, an enzyme reactant, a light absorbent, a fluorescent material, or a luminescent material.

According to another aspect of the present invention, there is provided a method of analyzing a biological sample characterized by injecting a sample into the membrane sensor as described above to measure an analyte.

The method of analyzing a biological sample as described above may include measuring electrochemical signals between multiple channels of the membrane sensor.

Advantageous Effects

The membrane sensor according to the present invention may enable mass-production of sensors and secure reliability of detection by forming the plurality of channels on the membrane by a simple method.

[Detailed Description of Main Elements]

| | |
|---|---|
| 10: membrane | 11: sample pad |
| 12: conjugation pad | 13: absorption pad |
| 14: lower substrate | 15: anti-CRP polyclonal antibody |
| 16: anti-mouse IgG | 20: hydrophobic ink |
| 30: paraffin ink | |

BEST MODE

The present invention relates to a method for manufacturing a multiple channel membrane sensor characterized by forming multiple channels on a membrane using a screen printing method.

Figure 1:
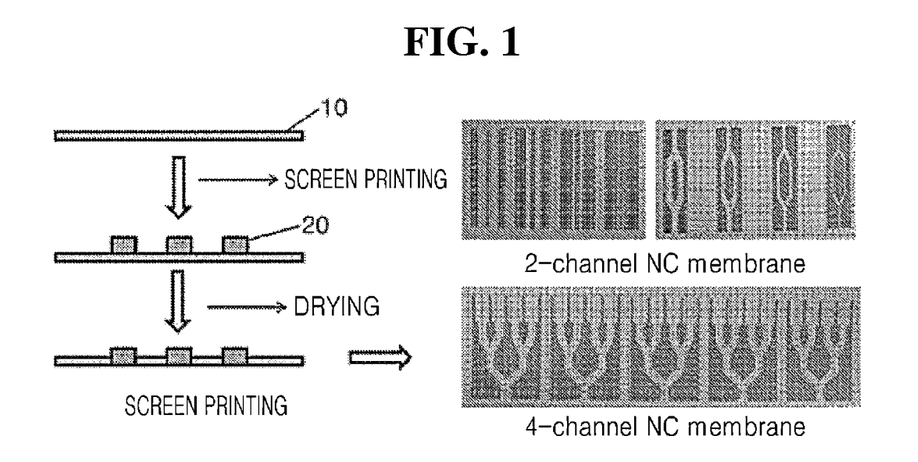
FIG. 1 is a view showing a process of forming multiple channels on a membrane using a screen printing method according to the present invention.

FIG. 1 is a view schematically showing a process of a multiple channel membrane sensor according to an exemplary embodiment of the present invention.

First, as a membrane 10, any membrane shaped material may be used as long as it may implement a lateral flow so as to confirm the desired chemical or biological reaction results simultaneously with serving as a path through which a biological sample is transferred. More preferably, a membrane made of a material selected from nitrocellulose, nylon, polysulfone, polyethersulfone, and polyvinylidene fluoride (PVDF) may be used, but is not limited thereto. The material may be suitably selected from materials capable of implementing a lateral flow of a liquid sample by those skilled in the art.

Hydrophobic ink 20 may be printed on the membrane using a screen printing method. The screen printing may be performed by the method widely known in the art. For example, a printer for performing the screen printing may be composed of a fine mesh provided with an opening part forming a predetermined pattern, a squeegee for applying hydrophobic ink, and a stage module supporting the membrane at a lower portion of the mask. The screen-printed ink is applied onto the membrane at a thickness of 5 to 10 μm, and the applied ink may be partially deposited through pores of the membrane.

Any kind of hydrophobic ink may be used as long as it may not be mixed with an injection sample to serve as a channel inducing a flow of the sample, but preferably, a silver paste, a carbon paste, a platinum paste, a ceramic paste, wax, or the like, may be used. Among them, the silver paste may be most preferable.

In the case of printing the ink in a desired shape using the screen printing method and then drying the printed ink, multiple channels enabling movement of a sample may be formed.

In addition, it is preferable that the hydrophobic ink further contains an organic solvent. The reason is that since the membrane has a property of being dissolved in an organic solvent, in the case of printing the hydrophobic ink together with a suitable organic solvent, a hydrophobic property of the ink may be increased, thereby making it possible to prevent the sample from spreading around patterns. Further, in the case of using the organic solvent, efficiency of the printed ink penetrating through the pore of the membrane is increased, such that a hydrophobic property of the formed channel may be increased.

As the organic solvent, alcohols having 1 to 6 carbon atoms, dimethylformamide (DMF), dimethyl sulfoxide (DMSO), acetone, or the like may be used, but it is preferable that the organic solvent is suitable adjusted according to the material of the used membrane. In addition, 1 to 80 parts by weight, more preferably, 5 to 50 parts by weight of the organic solvent may be used based on 100 parts by weight of a hydrophobic solvent.

Figure 2:
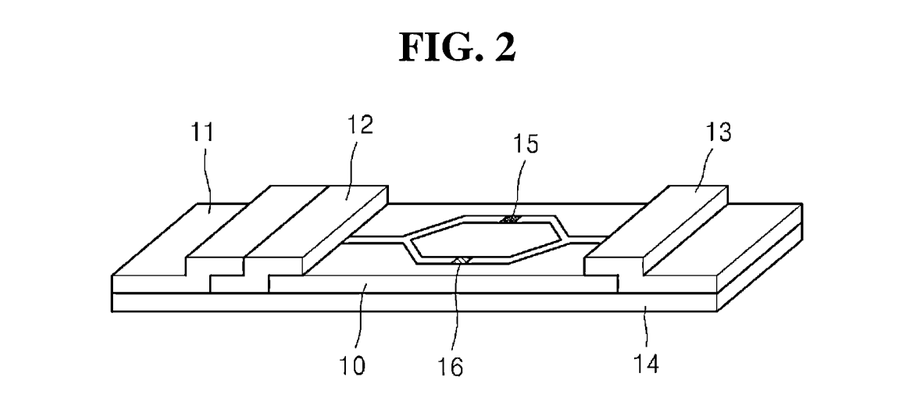
FIG. 2 shows a configuration of a membrane sensor according to an exemplary embodiment of the present invention.

Further, at the time of drying the screen-printed membrane, it is preferable that the membrane is dried in an oven at 50 to 200° C. for 10 minutes to 3 hours. Meanwhile, the membrane sensor according to the present invention may be configured to include a sample pad 11, a conjugation pad 12, an absorption pad 13, and a lower substrate 14, which are components of a general strip bio sensor, as shown in FIG. 2. In the present invention, the sample pad serves to allow an injected liquid sample to be developed in a reaction membrane, and the absorption pad serves to absorb sample developed in the reaction membrane. A kind of material of the sample pad or absorption pad is not limited as long as it may absorb the liquid sample, but preferably, the sample pad or absorption pad may be made of a material such as cellulose, polyester, polypropylene, or glass fiber.

Further, in the present invention, as the conjugation pad, a pad treated with a signal generation material or a conjugate of a material selectively binding to an analyte such as a detection antibody and a signal generation material may be used.

In the case in which the signal generation material is applied and dried onto the conjugation pad, for example, when the signal generation material is an enzyme, an enzyme substrate, or a chemiluminescent material, the analyte may be measured through signals of the signal generation material caused by an enzyme reaction by injecting the sample after injecting or adsorbing an enzyme substrate or enzyme reacting with the signal generation material onto the membrane in advance together with a receptor. In the case in which the conjugate of the material selectively binding to the analyte and the signal generation material is applied and dried onto the conjugation pad, the analyte may be measured through signals of the signal generation material caused by a selective reaction between the receptor and the analyte.

In the present invention, as a material of the conjugation pad, any material may be used as long as the conjugate may be easily detached from the conjugation pad in the case in which the conjugation pad is wet by a liquid after applying and drying the conjugate, and any conjugation pad may be used as long as it is generally used in a LFA system. That is, the membrane materials such as nitrocellulose, nylon, polysulfone, polyethersulfone, or polyvinylidene fluoride (PVDF) may be also used as well as materials such as cellulose, polyester, polypropylene, or glass fiber.

Meanwhile, the signal generation material may be metal nanoparticles, aquantum dot nanoparticles, magnetic nanoparticles, an enzyme, an enzyme substrate, an enzyme reactant, a light absorbent, a fluorescent material, or a luminescent material. In the case in which the signal generation material is metal nanoparticles, the analyte may be detected through a change in color of the metal nanoparticles caused by a selective reaction between the receptor and the analyte, and the analyte may be quantitatively analyzed by measuring absorbance, electric conductivity, or the like, of a conjugate of the analyte selectively binding to the receptor on the membrane and the metal nanoparticles. These metal nanoparticles may be, for example, gold nanoparticles, silver nanoparticles, copper nanoparticles, or the like, but is not limited thereto.

In the case in which the signal generation material is the enzyme, the enzyme substrate, or the enzyme reactant, the analyte or receptor and the enzyme, enzyme substrate, or enzyme reactant react with each other by a selective reaction between the receptor and the analyte to cause an enzyme reaction such as an oxidation reduction reaction, or the like. In this case, the analyte may be detected by measuring absorbance, fluorescence, luminescence, or the like, of the product produced by the enzyme reaction. The enzyme as described above may be, for example, glucose oxidase, glucose dehydrogenase, alkali phosphatase, peroxidase, or the like, but is not limited thereto. The enzyme substrate may be, for example, glucose, hydrogen peroxide, or the like, but is not limited thereto.

In addition, as the signal generation material, a light absorbent, a fluorescent material, or a luminescent material known in the art may be used, and a specific kind thereof may be suitably selected by those skilled in the art.

In the present invention, the sample injected through the sample pad may be an arbitrary sample containing or not containing the analyte and mean a fluid capable of flowing from the sample pad to the absorption pad through the reaction membrane. More specifically, the sample means blood, serum, or a liquid sample including a specific analyte (DNA, protein, chemical, a toxic material, or the like).

Further, the present invention relates to a method of analyzing a biological sample characterized by injecting a sample into a multiple channel membrane sensor formed by printing hydrophobic ink as described above to measure an analyte using an immune reaction, or the like.

Independent measurement may be performed at each of the channel by fixing detection antibodies, or the like, to the multiple channels, respectively. That is, for example, in the case of a general LFA strip, an unreacted gold nanoparticle-antibody complex first passes through a portion to which the detection antibody is fixed and then binds to anti-mouse IgG to indicate a control signal. As a result, in the case in which a concentration of an antigen is high, a result of an anti-mouse IgG region is indicated to be low, but in the case the sensor according to the present invention, antigen-antibody reactions are each independently carried out in each of the multiple channels, and a control channel is not affected by a concentration of an antigen unlike the channel to which the detection antibody is fixed. Therefore, more reliable results may be secured.

In addition, the sample may be analyzed by measuring electrochemical signals between the multiple channels of the membrane sensor using electric properties of the screen-printed hydrophobic ink. More specifically, in the case of injecting an experimental solution containing a sample into multiple channels between electrodes and applying a predetermined voltage or current to the electrodes facing each other, a concentration of a detection material in the injected sample may be measured by measuring a current or resistance reflecting electric properties of the experimental solution present between the electrodes. For example, in the case of using an experimental solution having large specific resistance as compared to the detection material, as the concentration of the detection material is increased, a lower current may flow in the experimental solution due to an increase in resistance. Therefore, the concentration of the detection material may be measured by measuring the current flowing between two electrodes.

The above-mentioned and additional aspects of the present invention will be more clearly described through preferable Examples described with reference to the accompanying drawings. Hereinafter, the present invention will be described through these Examples so as to be easily understood and reproduced by those skilled in the art.

However, these Examples are only to illustrate the present invention, and those skilled in the art will appreciate that these Examples are not to be construed as limiting a scope of the present invention.

Example 1: Manufacturing of Multiple Channel Membrane by Screen Printing

A silver paste as hydrophobic ink was screen printed onto a nitrocellulose membrane (Millipore, 180 sec Nitrocellulose, 4 mm×25 mm) at a thickness of 5 to 10 μm so that four channels were formed as shown in FIG. 1. Then, the silver paste printed membrane was dried at room temperature for 15 minutes and then treated at a drying oven at 100° C. for 1 hour, thereby finally obtaining a multiple channel membrane.

Examples 2 and 3: Screen Printing Using Organic Solvent

A membrane was manufactured by the same method as in Example 1 except for performing a screen printing process after mixing ethanol with the silver paste so that contents of ethanol were 5 wt % and 10 wt %, respectively.

A phosphate buffer saline (PBS, Gibco, USA) solution containing 1% (w/v) protease-free bovine serum albumin (BSA, Fitzerald) was flowed into the prepared multiple channel membrane, and flows spread around the patterns were confirmed. The results were shown in FIG. 3.

Figure 3:
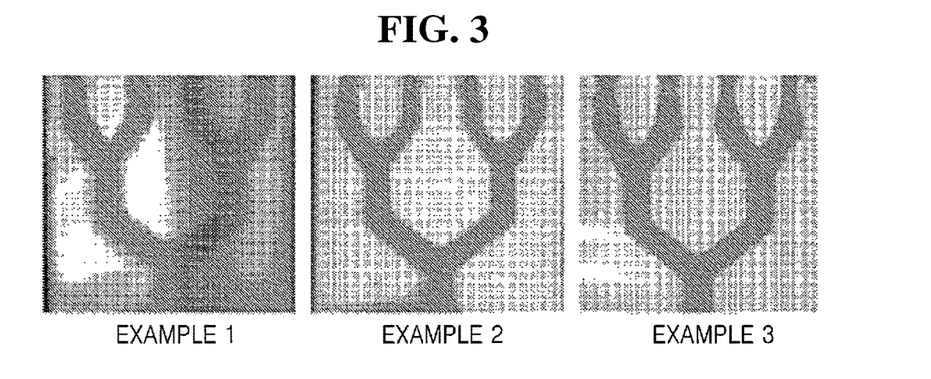
FIG. 3 is a photograph for confirming a flow spread around a pattern in the case of flowing a phosphate buffer saline (PBS) solution onto screen-printed membranes of Examples 1 to 3 (Example 1: ethanol free, Example 2: 5 wt % of ethanol, Example 3: 10 wt % of ethanol).

As shown in FIG. 3, it may be appreciated that in the case of the pattern formed by printing the silver paste to which ethanol was added, a solution spread around the channel was significantly decreased as compared to the pattern formed by printing the silver paste to which ethanol was not added. Particularly, in the case in which 10 w % of ethanol was added, flows spread around the pattern were almost nonexistent. Generally, since the nitrocellulose membrane has a property of being dissolved in ethanol, it may be considered that when the concentration of ethanol is suitably adjusted, the silver paste is invaded, such that the hydrophobic property is increased.

Example 4: Measurement of C-Reactive Protein (CRP) in Human Serum Using Biosensor 4-1. Synthesis of Gold-Nanoparticle-Antibody Conjugate 0.1 mL of 0.1M boric acid buffer (pH 8.5) was put into 1 mL of gold nanoparticle colloid solution (20 nm, BBInternational, GB) and then 10 μl of anti-CRP antibody (Abcam, 1 mg/mL) was added thereto, followed by reaction for 30 minutes. After the reaction, 0.1 mL of a solution obtained by dissolving 1% (w/v) protease-free bovine serum albumin (BSA, Fitzerald) in phosphate buffer saline (PBS, Gibco, USA) was added thereto, followed by reaction at 4° C. for 60 minutes. After the reaction, the reactant was centrifuged at 4° C. and 10,000 rpm for 20 minutes, and the resultant was purified and recovered by putting 1 mL of BSA solution (1 mg/mL) dissolved in 10 mM PBS three times, thereby synthesizing a gold nanoparticle-antibody conjugate. After the synthesized gold nanoparticle-antibody conjugate was concentrated 2.5 times, the concentrated conjugate was injected by 10 μL into a conjugation pad (fusion 5, whatman) cut at a size of about 7×4 mm and then dried.

4-2. Manufacturing of Membrane

A silver paste as hydrophobic ink was screen printed onto a nitrocellulose membrane (Millipore, 180 sec Nitrocellulose, 7 mm×25 mm) at a thickness of 10 μm so that two channels were formed as shown in FIG. 2.

Then, the silver paste printed membrane was dried at room temperature for 15 minutes and then treated at a drying oven at 100° C. for 1 hour, thereby finally obtaining a multiple channel membrane.

A biosensor as shown in FIG. 2 was configured using the membrane, a sample pad (glass fiber, 7 mm×7 mm), an absorption pad (glass fiber, 7 mm×10 mm), and the prepared conjugation pad.

1 μL of An anti-CRP polyclonal antibody 15 was fixed to one channel of two channels formed as describe above and 1 μL of anti-mouse IgG 16 was fixed to the other channel at a concentration of 1 mg/ml, respectively.

Then, 50 μl of solutions obtained by dissolving CRP in human serum (CRP-free serum) at the concentration of 0, 1, 10, 100, and 1000 ng/mL were injected into sample pad, respectively. After 3 minutes, absorbance was measured at each of the channels.

Figure 4:
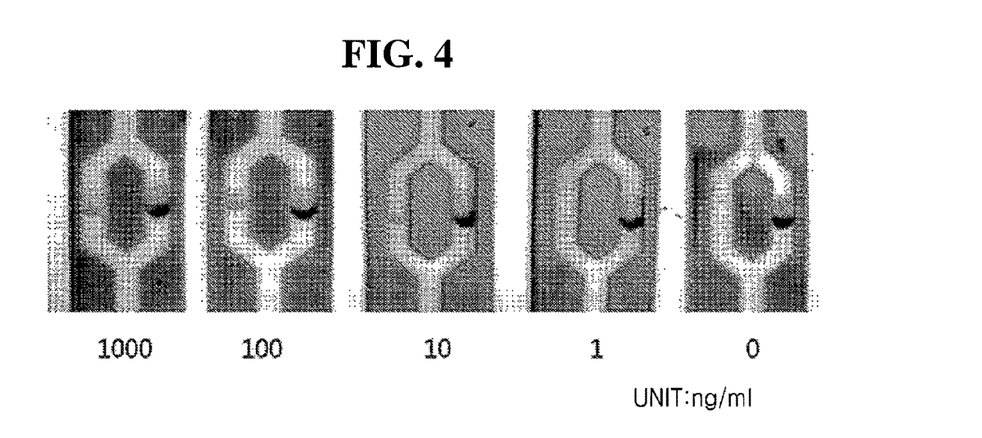
FIG. 4 is a photograph showing a sensing result according to a concentration of a C-reactive protein (CRP) antigen in Example 4.
Figure 5:
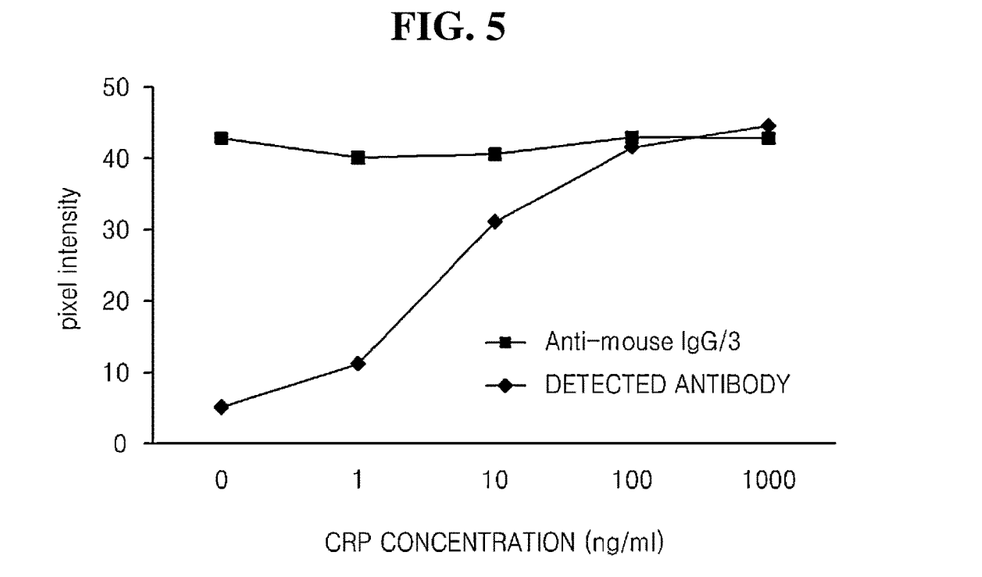
FIG. 5 is a graph for comparing absorbance of each of the channels according the concentration in Examples 4.

Sample injection result photographs were shown in FIG. 4, and absorbance measured at each of the channels were compared with each other in FIG. 5.

As shown in FIGS. 4 and 5, it may be confirmed that high reaction activity was shown regardless of the concentration of CRP at all of the control regions (right, portions to which the anti-mouse IgG was fixed), but at the test regions (left, portions to which the anti-CRP polyclonal antibody fixed), as the concentration of CRP was increased, the signal was also increased.

Figure 6:
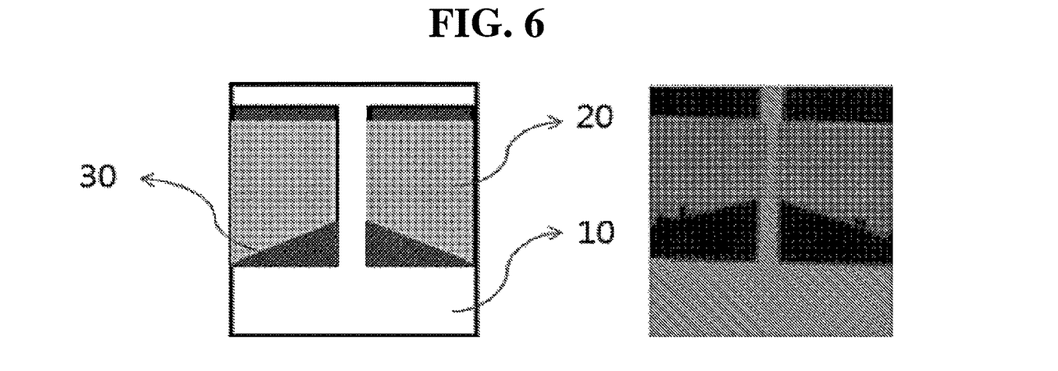
FIG. 6 is a mimetic view and a photograph of a sensor for measuring electrochemical light signals in a screen-printed membrane sensor in Example 5.

Example 5: Measurement of Electrochemical Luminescent Signal in Strip Sensor Screen Printed with Silver Paste Using Ruthenium Tris-bipyridine 5-1. Manufacturing of Sensor Channels were printed onto a nitrocellulose membrane (Millipore, 90 sec Nitrocellulose, 12 mm×10 mm) by an interval of 1.1 mm using a printer using paraffin solid ink and treated at 100° C. for 1 minute, such that paraffin was impregnated into the membrane. Electrodes were printed on the manufactured membrane using a silver paste by the method of Example 1 so as to have a screen interval of 500 μm as shown in FIG. 6, and then dried at room temperature for 3 hours. After the drying was completed, a copper wire was bonded onto a surface of each of the electrodes between two channels using a DOTITE D-500 conductive silver paint (Fujikura Kasei Co Ltd), and then each of the electrodes was connected to CompactStat (Ivium Technologies) through the copper wire.

5-2. Measurement of Electrochemical Luminescent Signal

After 1 mg of ruthenium tris-bipyridine was dissolved in 100 μl of DMSO, 5M tripropyl amine was dissolved in PBS buffer solution, and the obtained solutions were diluted 100 times in 10 mM PBS buffer, respectively. The diluted solutions were mixed at a volume ratio of 1:1, thereby preparing a reaction solution. After injecting 20 μl of the prepared reaction solution into a lower end portion of the membrane of the manufactured sensor to pass between the channels, a voltage of 1.7V, 2.5V, and 4V was applied for 160 seconds, respectively. In this case, a current was measured per 1 second, and at the same time, a chemical luminescent signal was measured. The chemical luminescent signal was measured using LAS3000 (Fujifilm).

Figure 7:
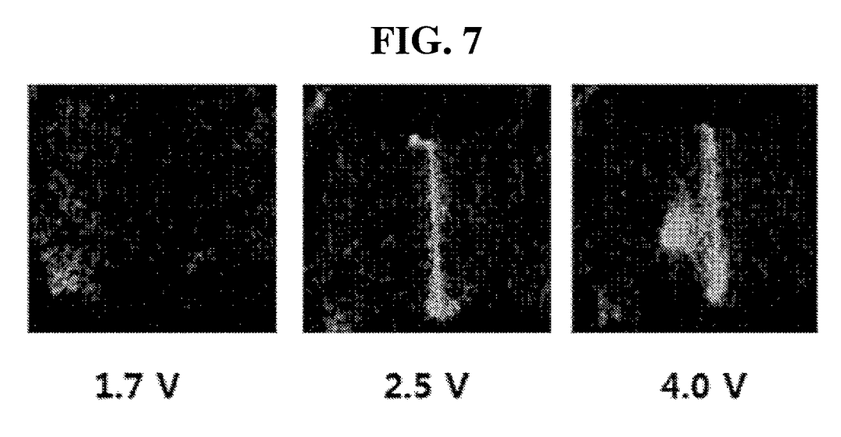
FIG. 7 is a photograph measuring chemical light signals according to an applied voltage in Example 5.
Figure 8:
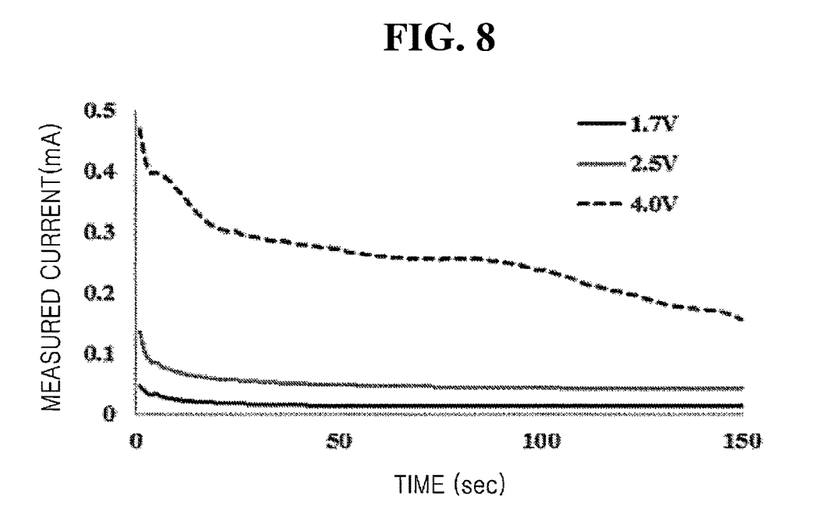
FIG. 8 is a comparison graph obtained by measuring a current change depending on the applied voltage according to the time in Example 5.

FIG. 7 shows photographs obtained by measuring the chemical luminescent signal through the above-mentioned process, and FIG. 8 is a comparison graph obtained by measuring a current change depending on the applied voltage according to the time. As shown in FIGS. 7 and 8, it may be confirmed that as the applied voltage was increased, the chemical luminescent signal and the measured current were increased. This result shows that measurement may be performed using the electric properties of the silver paste pattern manufactured according to the present invention.

As a result, it may be confirmed that the antigen may be easily measured according to the concentration using a multiple immune chromatograph by the biosensor according to the present invention. Further, it may be confirmed that the electrochemical luminescent signal may be measured using electric properties of a screen printed paste.

Although the present invention has been described in detail based on particular features thereof, and it is obvious to those skilled in the art that these specific technologies are merely preferable embodiments and thus the scope of the present invention is not limited to the embodiments. Therefore, the substantial scope of the present invention is defined by the accompanying claims and equivalent thereof.

The invention claimed is:

1. A method for manufacturing a sensor using a screen-printing, the method comprising:
   screen printing hydrophobic ink at a thickness of 5 to 10 μm onto a membrane in which a water soluble sample flows to form a pattern comprising multiple channels, wherein
   the hydrophobic ink comprises one or more of a silver paste, a carbon paste, a platinum paste, a ceramic paste, or a wax,
   the hydrophobic ink comprises one or more organic solvents selected from alcohols having 1 to 6 carbon atoms, dimethylformamide (DMF), dimethyl sulfoxide (DMSO), or acetone, and
   the membrane comprises one or more of nitrocellulose, nylon, polysulfone, polyethersulfone, or polyvinylidene fluoride (PVDF).

2. A sensor, comprising:
   a membrane; and
   multiple channels formed by screen printing hydrophobic ink having a thickness of 5 to 10 μm on a surface of the membrane, wherein
the membrane is configured to accommodate a lateral flow of a water soluble sample,
the hydrophobic ink comprises one or more of a silver paste, a carbon paste, a platinum paste, a ceramic paste, or a wax,
the hydrophobic ink comprises one or more organic solvents selected from alcohols having 1 to 6 carbon atoms, dimethylformamide (DMF), dimethyl sulfoxide (DMSO), or acetone, and
the membrane comprises one or more of nitrocellulose, nylon, polysulfone, polyethersulfone, or polyvinylidene fluoride (PVDF).

3. The sensor of claim 2, further comprising a sample pad, a conjugation pad, and an absorption pad on the membrane.

4. The sensor of claim 3, wherein the sample pad or the absorption pad comprises one or more of cellulose, polyester, polypropylene, or a glass fiber.

5. The sensor of claim 3, wherein the conjugation pad comprises one or more of cellulose, polyester, polypropylene, glass fiber, nitrocellulose, nylon, polysulfone, polyethersulfone, or polyvinylidene fluoride (PVDF).

6. The sensor of claim 3, wherein the conjugation pad is treated with a signal generation material or a conjugate of a material selectively binding to an analyte and the signal generation material.

7. The sensor of claim 6, wherein the signal generation material comprises one or more of metal nanoparticles, quantum dot nanoparticles, magnetic nanoparticles, an enzyme, an enzyme substrate, an enzyme reactant, a light absorbent material, a fluorescent material, or a luminescent material.

8. A method of analyzing a biological sample, the method comprising:
injecting the biological sample into a sensor comprising a membrane and multiple channels formed by screen printing hydrophobic ink having a thickness of 5 to 10 μm on a surface of the membrane; and
measuring one or more analytes of the biological sample,
wherein
the hydrophobic ink comprises one or more of a silver paste, a carbon paste, a platinum paste, a ceramic paste, or a wax,
the hydrophobic ink comprises one or more organic solvents selected from alcohols having 1 to 6 carbon atoms, dimethylformamide (DMF), dimethyl sulfoxide (DMSO), or acetone, and
the membrane comprises one or more of nitrocellulose, nylon, polysulfone, polyethersulfone, car polyvinylidene fluoride (PVDF).

9. The method of analyzing the biological sample of claim 8, further comprising measuring electrochemical signals between the multiple channels of the sensor.

* * * * *